(12) United States Patent
Brucato et al.

(10) Patent No.: US 11,019,916 B2
(45) Date of Patent: Jun. 1, 2021

(54) SINGLE DOSE PACKAGE WITH APPLICATOR

(71) Applicant: Centrix, Inc., Shelton, CT (US)

(72) Inventors: Robert Brucato, Cheshire, CT (US); William P. Dragan, Orange, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 16/718,386

(22) Filed: Dec. 18, 2019

(65) Prior Publication Data

US 2020/0121070 A1    Apr. 23, 2020

Related U.S. Application Data

(63) Continuation of application No. PCT/US2018/037562, filed on Jun. 14, 2018.

(60) Provisional application No. 62/522,766, filed on Jun. 21, 2017.

(51) Int. Cl.
*A46B 11/00*    (2006.01)
*A46B 17/02*    (2006.01)
*A61C 19/06*    (2006.01)

(52) U.S. Cl.
CPC ........ *A46B 11/0058* (2013.01); *A46B 11/002* (2013.01); *A46B 11/0086* (2013.01); *A46B 17/02* (2013.01); *A46B 2200/01* (2013.01); *A46B 2200/10* (2013.01); *A61C 19/063* (2013.01)

(58) Field of Classification Search
CPC ..... A46B 11/00; A46B 11/002; A46B 11/003; A46B 11/0058; A46B 11/0086; A46B 17/02; A46B 2200/01; A46B 2200/10; A61C 3/00; A61C 3/005; A61C 5/04; A61C 5/62; A61C 9/00; A61C 19/06; A61C 19/063; A61M 5/32; A61M 5/3213
USPC ....... 206/363–365; 211/85.13; 604/192, 198, 604/263
See application file for complete search history.

(56) References Cited

U.S. PATENT DOCUMENTS

| | | | |
|---|---|---|---|
| 2,747,574 A | 5/1956 | De Lorenzo | |
| 4,717,386 A * | 1/1988 | Simmons | A61M 5/3213 604/192 |
| 5,660,273 A | 8/1997 | Discko, Jr. | 206/229 |
| 5,860,806 A | 1/1999 | Pranitis, Jr. et al. | 433/80 |
| 6,203,503 B1 | 3/2001 | Kelly et al. | 600/573 |
| 6,957,958 B2 | 10/2005 | Rowe et al. | 433/89 |
| 7,112,062 B2 * | 9/2006 | Lee | A61C 5/60 206/63.5 |
| 7,476,046 B2 * | 1/2009 | Phillips | A46B 17/02 401/123 |
| 7,611,012 B2 * | 11/2009 | Ross | A61M 5/008 206/366 |
| 7,828,142 B2 | 11/2010 | Discko, Jr. | 206/229 |

(Continued)

*Primary Examiner* — Bryon P Gehman
(74) *Attorney, Agent, or Firm* — Fattibene and Fattibene LLC; Paul A. Fattibene

(57) ABSTRACT

A single dose package having a material chamber frangibly separable from a handle and concentric partial or semi-cylinders holding an applicator. An outer partial cylinder placed over an inner semi-cylinder encloses and holds an applicator. Moving the handle relative to the material chamber separates the handle from the material chamber to access a material contained within the material chamber. Different sizes and shapes of plugs sealing the material chamber selectively adjust the volume of the material chamber.

15 Claims, 11 Drawing Sheets

(56) References Cited

U.S. PATENT DOCUMENTS

| | | | |
|---|---|---|---|
| 8,852,158 B1 * | 10/2014 | Schaffer | A61M 5/3213 |
| | | | 604/192 |
| 9,446,198 B2 * | 9/2016 | Mercer | A61M 5/326 |
| 2004/0197730 A1 | 10/2004 | Rowe et al. | 433/80 |
| 2005/0123878 A1 | 6/2005 | Lee | 433/80 |
| 2006/0228159 A1 | 10/2006 | Phillips et al. | 401/132 |
| 2008/0217190 A1 | 9/2008 | Matsushige et al. | 206/63.5 |
| 2009/0264900 A1 | 10/2009 | Paz et al. | 606/138 |
| 2011/0024417 A1 | 2/2011 | Loukeris | 220/203.1 |
| 2011/0266165 A1 | 11/2011 | Pierson et al. | 206/63.5 |

* cited by examiner

SINGLE DOSE PACKAGE WITH APPLICATOR

RELATED APPLICATIONS

This application is a continuation of International Application PCT/US2018/037562, with an international filing date of Jun. 14, 2018, which claims the benefit of U.S. Provisional Application Nos. 62/522,766 filed Jun. 21, 2017, all of which are herein incorporated by reference.

FIELD OF THE INVENTION

The present invention relates in general to packaging of a material for application, and particularly to a single dose package having an applicator attached.

BACKGROUND OF THE INVENTION

There are many single dose or unit dose packages use for dispensing materials, such as medicaments. One such package is disclosed in U.S. Pat. No. 5,660,273 entitled "Single Patient Does Medicament Dispenser with Applicator" issuing to Discko on Aug. 26, 1997, which is herein incorporated by reference. Therein disclosed is a tray having wells for holding a medicament or material and an applicator for applying the medicament or material. A thin sheet or film covers and seals the material well and the applicator well, with the applicator handle extending from the tray. Another single dose or unit dose package is disclosed in U.S. Pat. No. 7,828,142 entitled "Single Patient Dose Medicament Dispenser with Applicator" issuing to Discko on Nov. 9, 2010, which is herein incorporated by reference. Therein disclosed is a single patient dose package for applying a material to an applicator. A material well is squeezed to dispense the material onto the applicator. Yet another single or unit dose applicator is disclosed in U.S. Pat. No. 6,957,958 entitled "Unit Dose Applicator with Material Chamber" issuing to Rowe et al on Oct. 25, 2005, which is herein incorporated by reference. Therein disclosed is an applicator having an applicator end portion and a material end portion. Upon separating the material end portion from the handle portion of the applicator, a container is form which is used to dip the applicator end portion of the applicator into. A single dose of material is integrally formed within the applicator and sealed.

While these prior unit or single dose packages worked well for the purposes for which they were intended, they are not without problems. It was often difficult to provide an adequate seal between the tray and the thin film cover sufficient to contain a liquid material. Additionally, upon opening the unit or single dose package the material contents would often spill or splash as the unit or single dose package was opened. It was also difficult to hold the applicator securely and hygienically within the unit or single dose package. Accordingly, there is a need for an improved unit or single dose package that solves the above mentioned problems.

SUMMARY OF THE INVENTION

The single unit dose package with applicator of the present invention comprises a stand having a material chamber formed therein adjacent a handle having a groove or frangible line placed there between. A semi-cylinder extends from the handle to hold an applicator. A partial cylinder rotatably covers the semi-cylinder protecting the applicator. The material chamber is opened by twisting the handle so as to break the frangible seal or line forming an opening to access the material with the applicator.

Accordingly, it is an object of the present invention to provide a single or unit dose dispenser that securely holds and protects an applicator.

It is another object of the present invention to securely seal a material therein.

It is an advantage of the present invention that a material chamber can be opened without splashing the material contained therein.

It is another advantage of the present invention that the applicator is easily removed.

It is a feature of the present invention that the material chamber is frangibly sealed adjacent a handle.

It is another feature of the present invention that the applicator is positioned to stand upright.

It is yet another feature of the present invention that concentric semi and partial cylinders our rotatable relative to each other securely holding the applicator within the single or unit dose package.

These and other objects, advantages, and features will become more readily apparent in view of the following detailed description.

DETAILED DESCRIPTION OF THE PREFERRED EMBODIMENTS

Figure 1A:
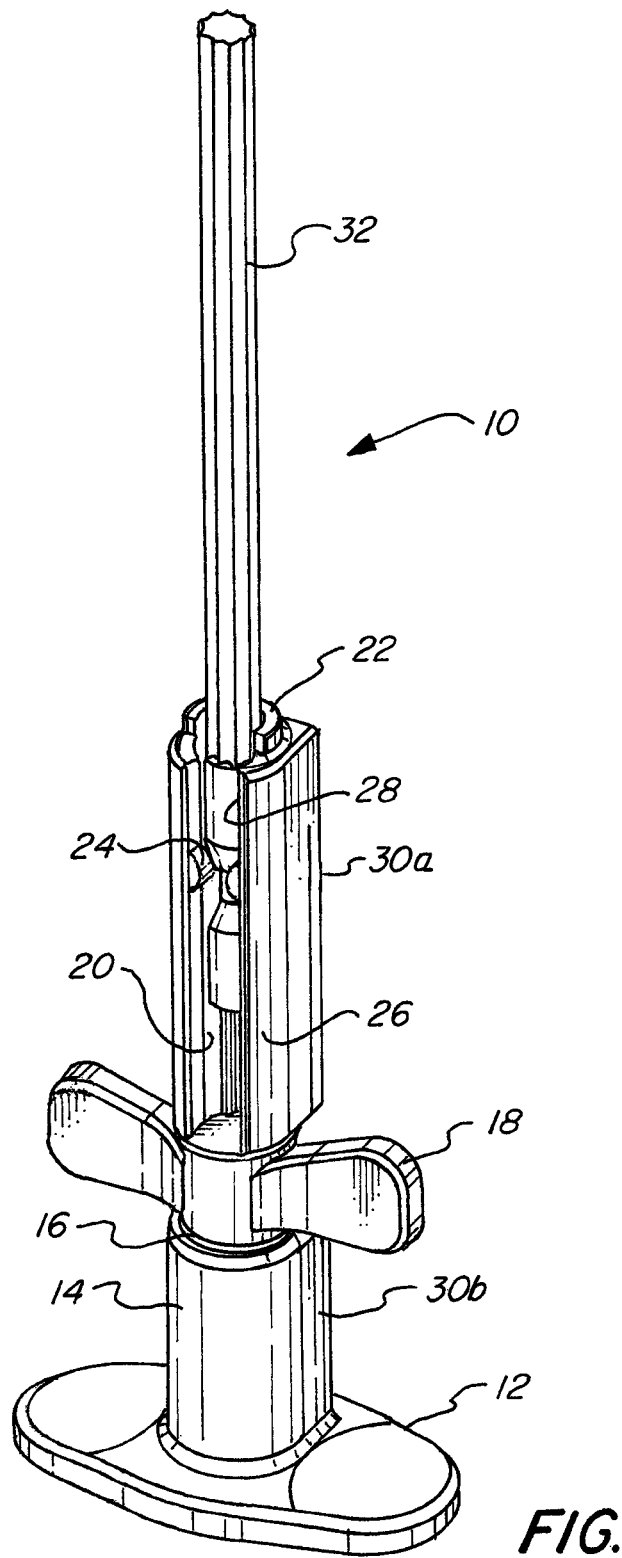
FIG. 1A is a front perspective view schematically illustrating the present invention.

FIG. 1A illustrates the single or unit dose package with applicator 10. The single unit dose package with applicator 10 stands upright and contains a singular or unit dose of material, such as a medicament, to be applied to a surface, such as a tooth surface used in a dental procedure. An applicator is also held securely and protected from contamination above the sealed material well The applicator is easily inserted and removed from the single dose package.

A stand 12 is attached to a material chamber 14. The material chamber 14 is frangibly attached to the handle 18.

A V-groove are frangible line 16 is placed between the material chamber 14 and the handle 18. Attached to the handle 18 is an inner semi-cylinder or half cylinder 20. At the distal end of the inner semi-cylinder 20 is a collar or flange 22. Protuberances 24 extend into the inner cavity of the inner semi-cylinder 20. An outer partial cylinder 26 having a longitudinal opening 28 is snapped over the inner semi-cylinder 20. The longitudinal opening 28 preferably extends less than 180° around the circumference of the partial cylinder 26 so as to permit a snap type fit over the inner semi-cylinder 20. The outer partial cylinder 26 is held between the handle 18 and the collar or flange 22. The outer partial cylinder 26 rotates on the inner semi-cylinder 20. When rotated into a closed position the outer partial cylinder 26 covers the open portion of the inner semi-cylinder 20 so as to securely hold and protect the applicator 32. An upper planar surface 30a is formed on the outer partial cylinder 26 and a lower planar surface 30b is formed on the material chamber 14. The upper and lower planar surfaces 30a and 30b provide a surface permitting indicia or writing to be placed thereon, such as identifying information about the material, directions of use, or other information.

Figure 1B:
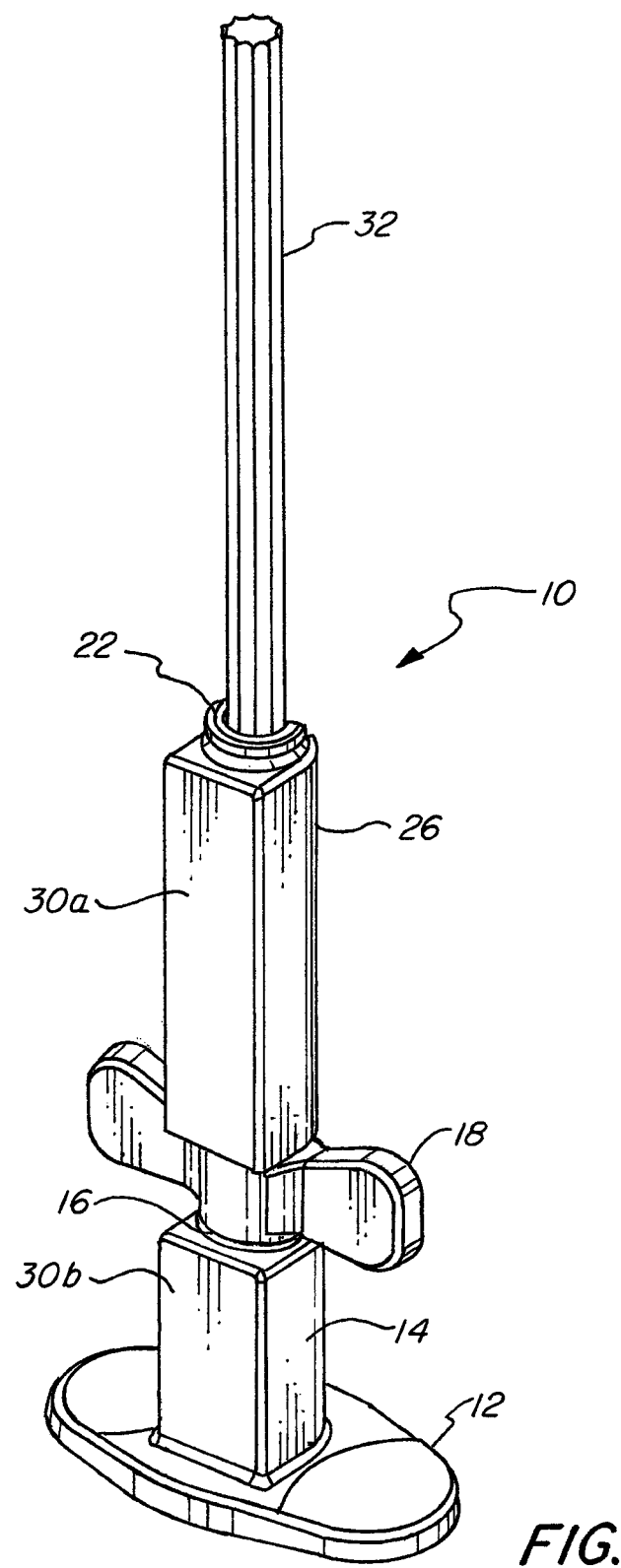
FIG. 1B is a rear perspective view schematically illustrating the present invention.

FIG. 1B more clearly illustrates the upper and lower planar surfaces 30a and 30b. The upper and lower planar surfaces 30a and 30b are illustrated as being rectangular, but may be any shape.

Figure 2:
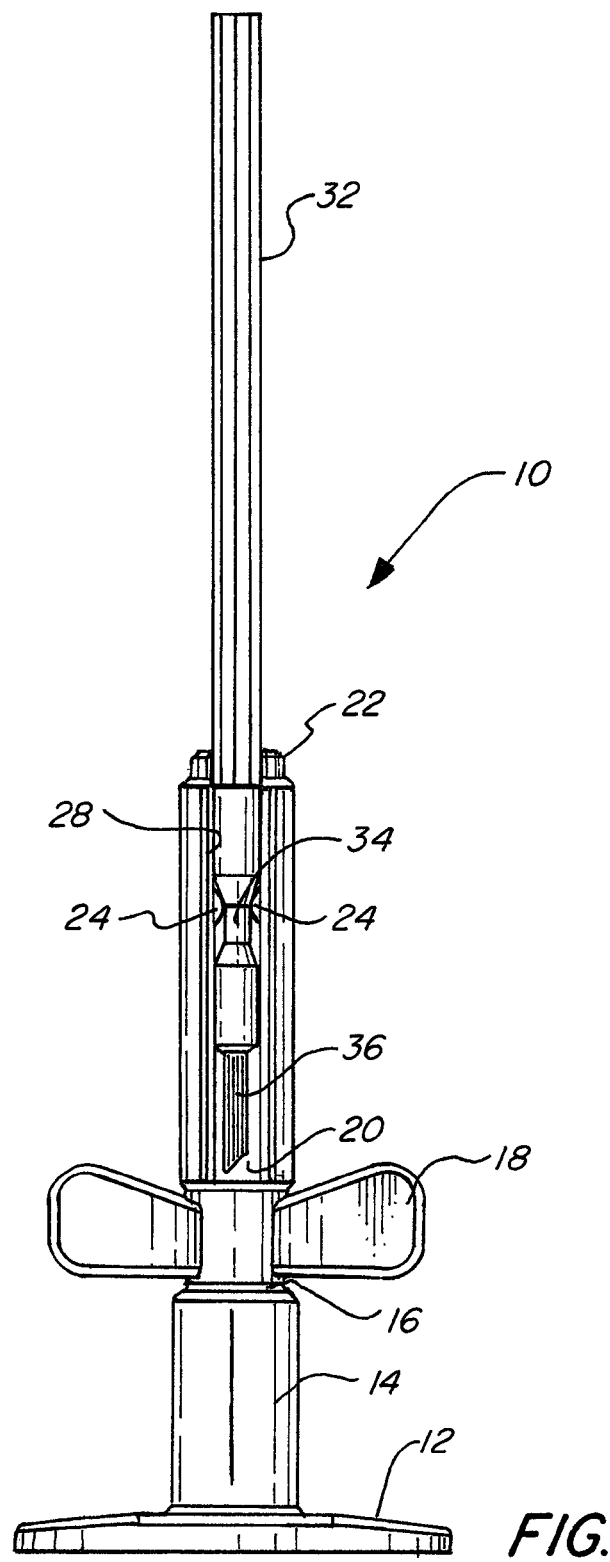
FIG. 2 is a front elevational view schematically illustrating the present invention.

FIG. 2 more clearly illustrates the interface or holding of the applicator 32 within the inner semi-cylinder 20. The applicator 32 is inserted through the longitudinal opening 28 into the inner semi-cylinder 20 and held therein by the protuberances 24. The protuberances 24 extend into a neck or indent 34 formed in the applicator 32. The applicator 32 has an applicator end or brush 36. The applicator end or brush 36 may be formed of bristles, foam, flock, or other equivalent material. Once the applicator 32 is placed into the inner semi-cylinder 20 the outer partial cylinder 26 is rotated relative to the inner semi-cylinder 20 so that the opening in the inner semi-cylinder 20 is covered by the outer partial cylinder 26. The holds and seals the applicator within the concentric inner semi-cylinder 20.

Figure 3:
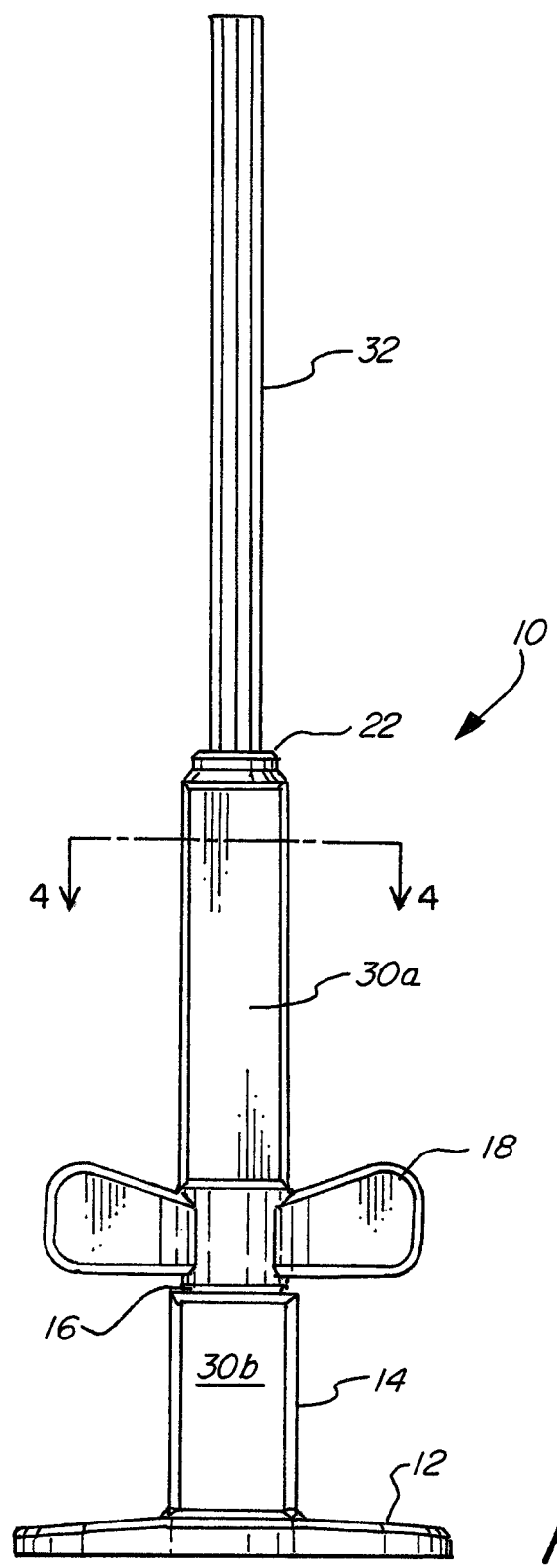
FIG. 3 is a rear elevational view schematically illustrating the present invention.

FIG. 3 clearly illustrates the single dose package with applicator 10 and the upper and lower planar surfaces 30a and 30b. The V-groove or frangible line 16 between the material chamber 14 and the handle 18 is also more clearly illustrated.

Figure 4:
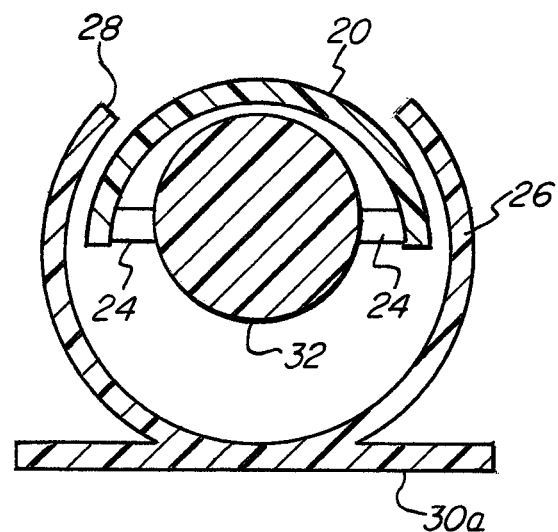
FIG. 4 is a lateral cross section taken along line 4-4 in FIG. 3.

FIG. 4 is a cross section taken along line 4-4 in FIG. 3. The relationship between the inner semi-cylinder 20 and the outer partial cylinder 26 is more clearly shown. The applicator 32 is held in position between the protuberances 24 within the inner semi-cylinder 20. The longitudinal opening 28 is placed over the inner semi-cylinder 20. Preferably the longitudinal opening 28 extends less than 180° around the circumference of the outer partial cylinder 26. The longitudinal opening 28 preferably has a cord therebetween that is less than the diameter of the inner semi-cylinder 20. This assures a snap type fit of the outer partial cylinder 26 onto the inner semi-cylinder 20.

Figure 5:
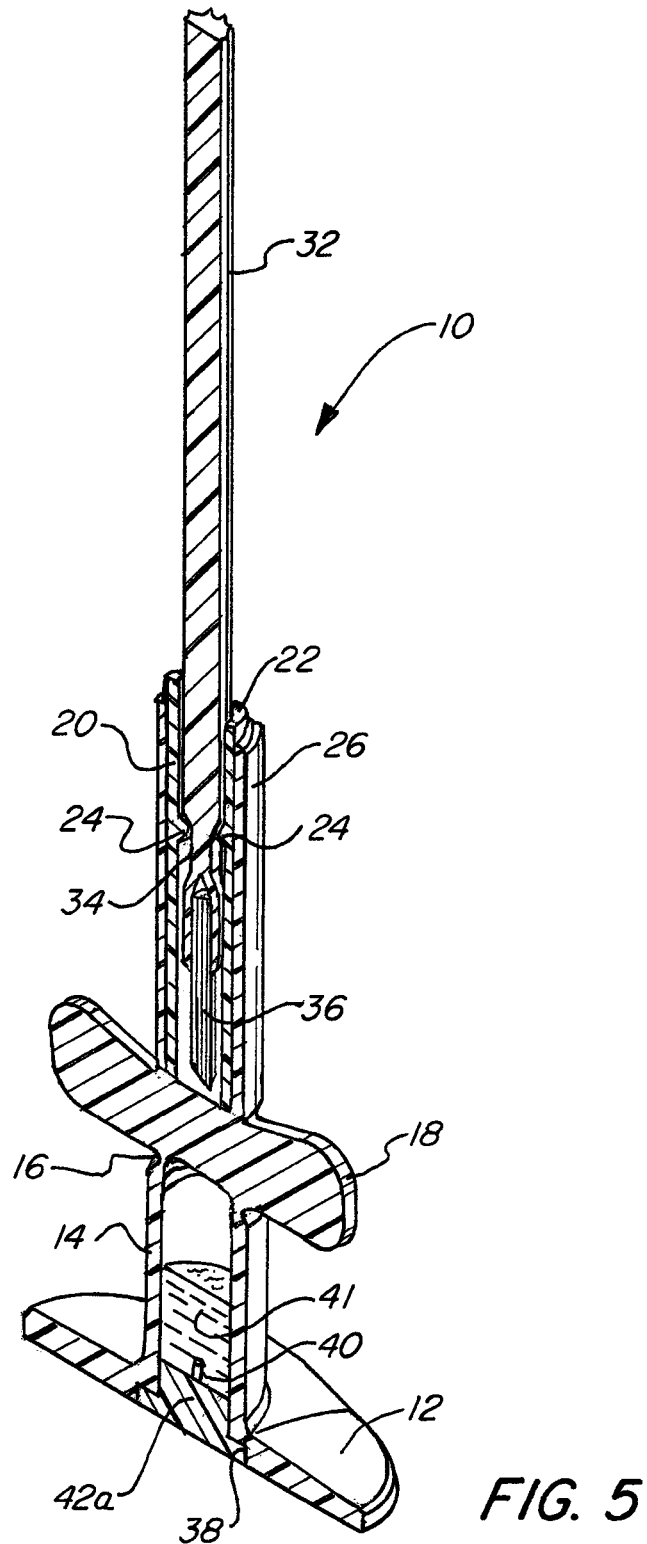
FIG. 5 is a longitudinal cross section of the present invention.

FIG. 5 is a longitudinal cross-section more clearly illustrating the construction of the present invention including the material chamber 14. Placed within the material chamber 14 is a material 41. The material 41 is preferably a liquid and may be a medicament used in a medical or dental procedure, as well as in any other desired application. A plug 42a is inserted into a plug recess 38. A vent 40 is formed in a sidewall of the material chamber 14. The vent 40 aids in the insertion of the plug 42 within the plug recess 38 by venting air from the material chamber 14 when the plug 42a is inserted. The vent preferably ends before the bottom of the stand 12 so that the material chamber 14 is completely sealed after the plug 42a is inserted into the plug recess 38. The plug 42a may be retained within the plug recess 38 by friction, glue, or a sonic weld. Preferably the plug is sonically welded to the stand 12 or the material chamber 14. The opening in the material chamber 14 adjacent the V-groove or frangible line 16 and the handle 18 is also more clearly illustrated. Accordingly, when the handle 18 is rotated or bent relative to the stand 12, the V-groove or frangible line 16 is broken providing an opening permitting access to the material 41 contained within the material chamber 14. The applicator may then be used to apply the material 41 contained within the material chamber 14 to a surface.

Figure 6:
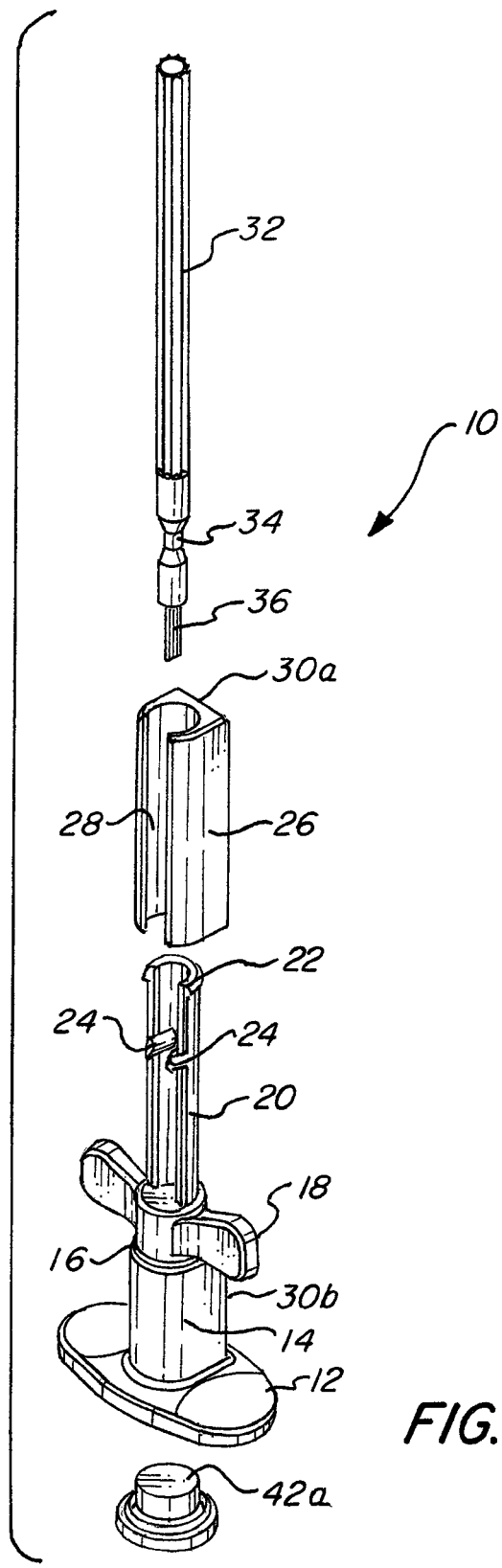
FIG. 6 it is an exploded view illustrating the components and assembly of the present invention.

FIG. 6 is an exploded view of the single dose package with applicator 10 of the present invention more clearly illustrating the components forming its construction. The outer partial cylinder 26 is placed over the inner semi-cylinder 20. With the longitudinal opening 28 of the outer partial cylinder 26 aligned with the open portion of the inner semi-cylinder 20 the applicator 32 can be inserted into the open portion of the inner semi-cylinder 20 with the neck 34 inserted between the protuberances 24 to securely hold the applicator 32 therein. Once inserted the outer partial cylinder 26 is rotated on the inner semi-cylinder 20 closing the open portion of the inner semi-cylinder 20. This structure securely holds the applicator within the inner semi-cylinder 20 and protects the applicator from contamination.

Figure 7A:
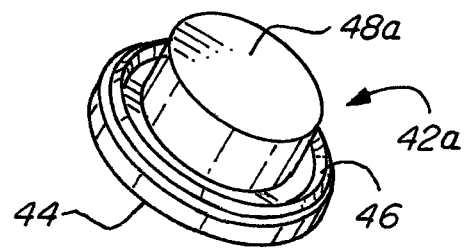
FIGS. 7A-C illustrate different size plugs used in the present invention.
Figure 7B:
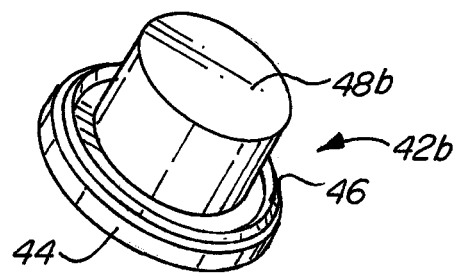
Figure 7C:
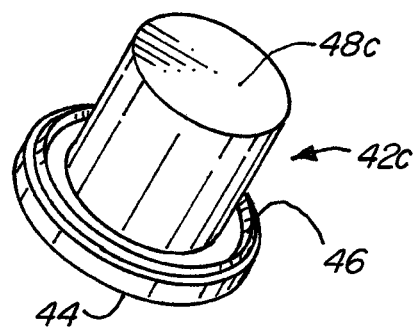

FIGS. 7A-C illustrate different length plugs which may be used for insertion into the plug recess 38, illustrated in FIG. 5. The different length plugs have inserts that permit the volume of the material chamber 14 to be changed or adjusted. For example, FIG. 7A illustrates plug 42a having a short insert 48a. The short insert 48a has a relatively short longitudinal length so that when inserted into the plug recess 38, illustrated in FIG. 5, the volume of the material chamber 14, illustrated in FIG. 5, will be relatively large. FIG. 7B illustrates plug 42b having a medium insert 48b. The medium insert 48b has a relatively longer longitudinal length so that when inserted into the plug recess 38, illustrated in FIG. 5, the volume of the material chamber 14, illustrated in FIG. 5, will be relatively smaller. FIG. 7C illustrates plug 42c having the longest insert 48c. The longest insert 48c has the longest longitudinal length so that when inserted into the plug recess 38, illustrated in FIG. 5, the volume of the material chamber 14, illustrated in FIG. 5, will be relatively the smallest. All of the plugs 42a, 42b, and 42c have a base 44 with a ridge 46 thereon. The ridge 46 facilitates sealing the material chamber with the plug using an ultrasonic weld.

By varying the longitudinal length of the inserts 48a, 48b, and 48c the volume of the material chamber 14, illustrated in FIG. 5, may be changed as desired. For example, depending upon the plug selected the material chamber volume may typically range from between 0.15 mL to 0.5 mL, as an example.

Figure 8A:
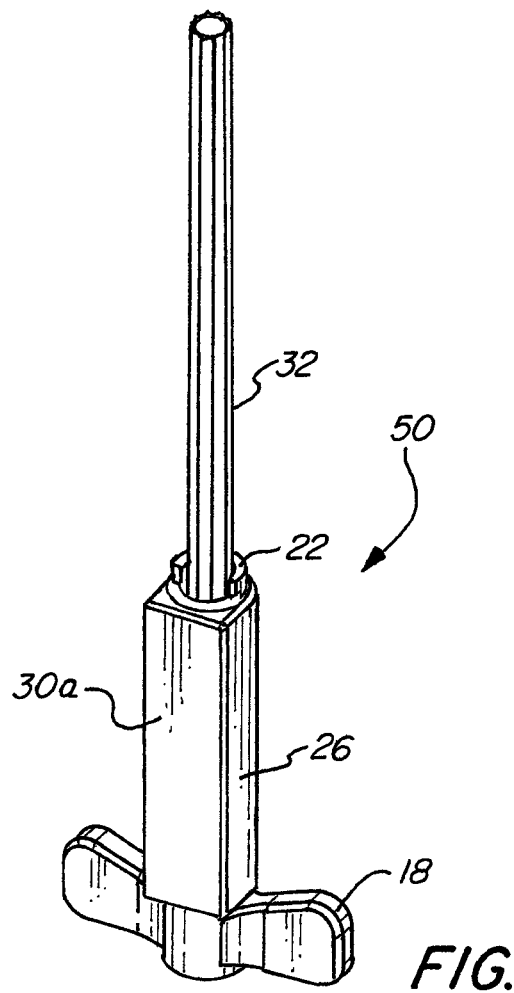
FIGS. 8A-B illustrate the opening of the material chamber and separation of the upper applicator assembly from the lower material chamber assembly.
Figure 8B:
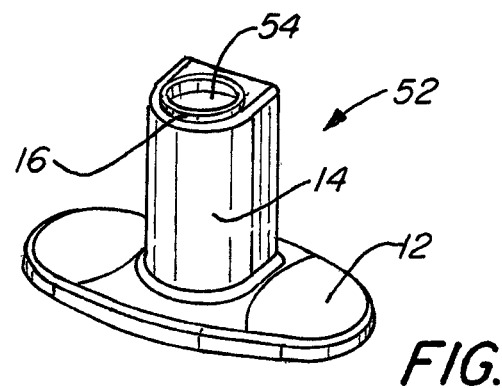

FIGS. 8A-B illustrates separation of the upper applicator assembly 50 from the lower material chamber assembly 52. By separating the upper applicator assembly 50 from the lower material chamber assembly 52 along the V-groove or frangible line 16, an opening 54 is formed in the material chamber 14. The material contained within material chamber 14 can then be accessed for applying to a surface with the applicator 32.

The configuration and structure of the present invention has the advantage that the stand 12 can be held securely on a flat surface while the handle 18 is twisted so as to separate the upper applicator assembly 50 from the lower material chamber assembly 52. This can be done without the stand 12 and material chamber 14 moving. This substantially reducing the possibility of splashing the material contained within the material chamber 14.

Figure 9:
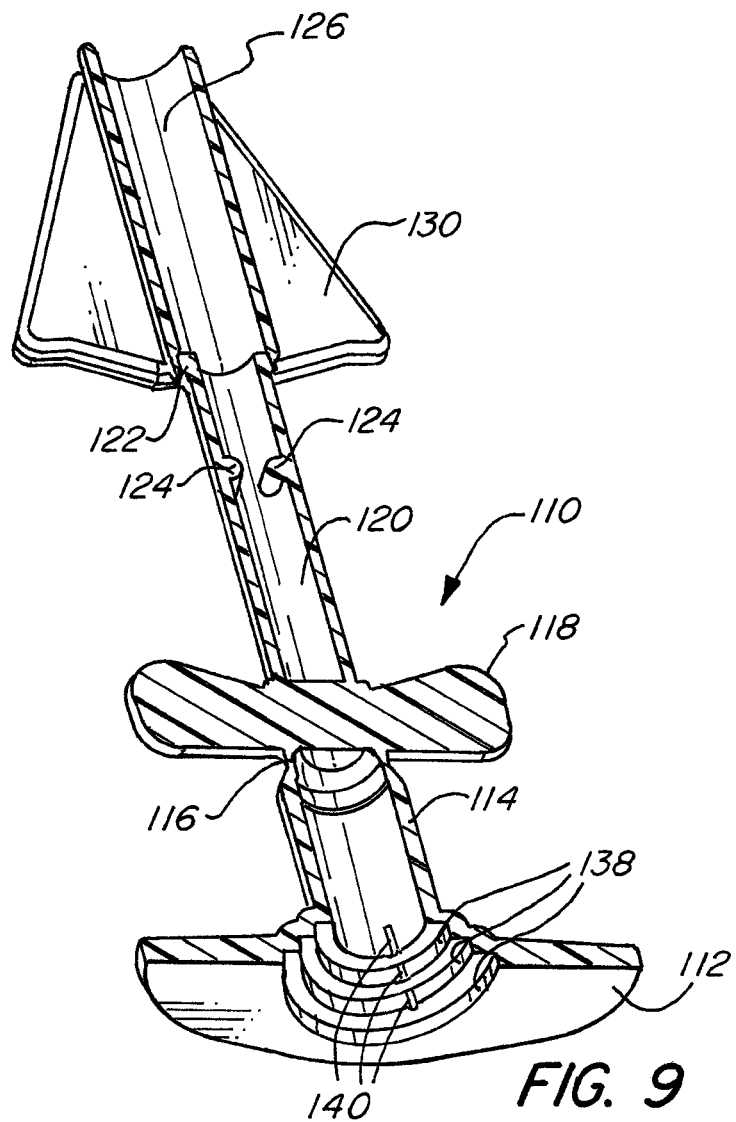
FIG. 9 is a cross section schematically illustrating another embodiment of the present invention having stepped plug recesses.
Figure 10A:
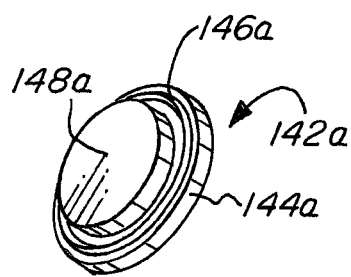
FIGS. 10A-B are perspective views schematically illustrating different diameter plugs.
Figure 10B:
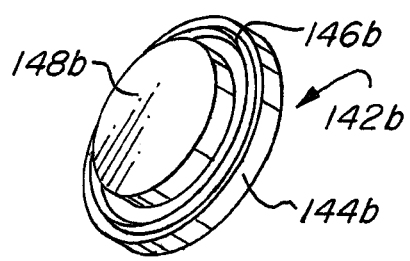

FIGS. 9 and 10A-B illustrate another embodiment of the invention. This embodiment has a different configuration for varying the volume of the material chamber. In this embodiment the single dose package with applicator 110 has a stand 112 and a material chamber 114. V-groove or frangible line 116 separates the material chamber 114 from the handle 118. Semi-cylinder 120 is attached to the handle 118 and has protuberances 124 therein. On the distal end of the semi-cylinder 120 is a collar or flange 122. The outer partial cylinder 126 is placed over the inner semi-cylinder 120, when assembled. A relatively large planar surface 130 permits additional indicia or writing to be placed thereon providing information to the user. Stand 112 has a plurality of steps plug recesses 138 formed therein. The sidewall surfaces of the step plug recesses 138 have vents 140 formed therein.

FIGS. 10A-B illustrate different diameter plugs to be inserted into the step plug recesses 138, illustrated in FIG. 9, permitting the volume of the material chamber 114, illustrated in FIG. 9, to be adjusted as desired. As an example, FIG. 10A illustrates a plug 142a having a base 144a with a small diameter and an insert 148a also with a small diameter. A rigid 146a is formed on the base 144a and is used to facilitate sealing the plug 142a by ultrasonic welding. Similarly, FIG. 10B illustrates a plug 142b having a base 144b with a relatively larger diameter and an insert 148b also with a relatively larger diameter. A rigid 146b is also formed on the base 144b and is used to facilitate sealing the plug 142b by ultrasonic welding.

Referring to FIG. 9 and FIGS. 10A-B the volume of the material chamber 114 may be changed by the insertion of different diameter plugs, 142a 142b onto the different diameter stepped plug recesses 138. Using a smaller diameter plug results in a smaller volume of the material chamber 114, as the smaller diameter plug is inserted further up the stepped plug recesses.

Figure 11A:
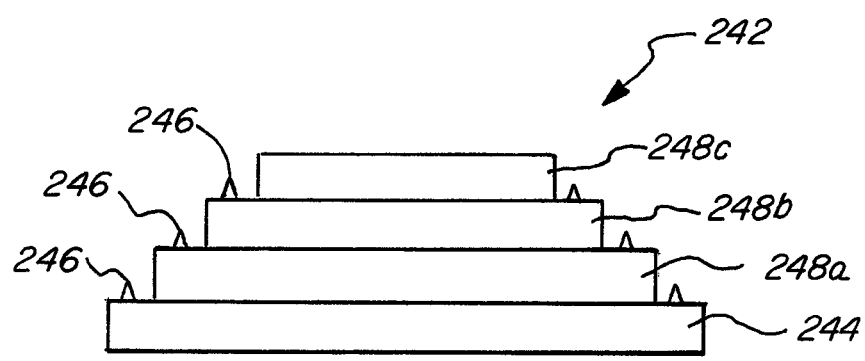
FIGS. 11A-B are elevational views schematically illustrating a multilevel plug.
Figure 11B:
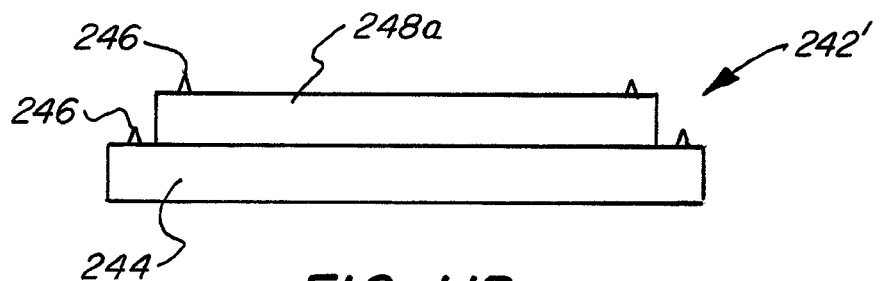

FIGS. 11A-B illustrate another type of plug that may be used so as to vary the volume of the material chamber 114, illustrated in FIG. 9. The advantage of this embodiment is that a single plug may be modified so as to provide the desired volume and that multiple seals may be used assuring the material chamber 114, illustrated in FIG. 9, will not leak. FIG. 11A illustrates a multilevel plug 242 having a base 244 with a plurality of different inserts 248a, 248b, 248c having different diameters formed thereon. FIG. 11B illustrates the multilevel plug 242' with the smaller diameter inserts 248c and 248b removed or cut away. Accordingly, when the multilevel plug 242 is inserted into the stepped plug recess 138, illustrated in FIG. 9, the volume of the material chamber 114, illustrated in FIG. 9, will be smaller than when the multilevel plug 242' is inserted into the stepped plug recess 138. The ridges 246 place on each level of the multilevel plugs 242 and 242' makes possible the use of multiple seal at each level. This embodiment also has the advantage of reducing material waste by preventing some quantity of material from being collected between the insert ant the sidewall of the material chamber.

The present invention provides an improved unit or single dose package that securely holds an applicator and that prevents spilling the material when opened. This makes applying a material to a surface easier. The present invention also permits the applicator to be replaced within the package and protected between applications of material.

While the present invention has been described with respect to various embodiments, various modifications may be made without departing from the spirit and scope of this invention.

What is claimed is:

1. A single dose package comprising:
   a stand;
   a material well attached to said stand;
   a handle frangibly attached to said material well;
   a first partial cylinder having an axis and a first longitudinal opening extending along the axis, said first partial cylinder attached to said handle;
   an applicator held within said first partial cylinder; and
   a second partial cylinder having a second longitudinal opening extending along the axis rotatably placed over said first partial cylinder, wherein said second partial cylinder is configured to cover the first longitudinal opening of said first partial cylinder when rotated about the axis of said first partial cylinder.

2. A single dose package as in claim 1 further comprising:
   a plug recess formed in said material well; and
   a plug placed in said recess sealing said material well.

3. A single dose package as in claim 2 wherein:
   said plug has an insert with a predetermined longitudinal length, whereby the predetermined longitudinal length of said insert is capable of being selected to adjust a volume of said material well.

4. A single dose package comprising:
   a stand;
   a material well attached to said stand;
   a handle frangibly attached to said material well;
   a first partial cylinder having an opening attached to said handle;
   an applicator held within said first partial cylinder; and
   a second partial cylinder rotatably placed over said first partial cylinder, whereby said second partial cylinder is capable of covering the opening of said first partial cylinder;
   a plug recess formed in said material well;
   a plug placed in said recess sealing said material well; and
   wherein said plug recess comprises a plurality of steps of different diameters.

5. A single dose package as in claim 4 wherein:
   said plug comprises a predetermined diameter, whereby the predetermined diameter is capable of being selected to adjust a volume of said material well.

6. A single dose package as in claim 4 wherein:
   said plug comprises a plurality of levels of different diameters, whereby at least one of the plurality of levels is capable of being removed to adjust a volume of said material well.

7. A single dose package comprising:
   a material chamber having an opening;
   a handle attached to said material chamber covering the opening;
   a frangible line placed between said material chamber and said handle;
   an inner semi-cylinder having an axis and a first longitudinal opening attached to said handle, said inner semi-cylinder having an inner surface and a distal end;
   a protuberance formed on the inner surface of said inner semi-cylinder;
   an applicator placed within said inner semi-cylinder and held by said protuberance;

a collar formed on the distal end of said inner semi-cylinder;

an outer partial cylinder having a second longitudinal opening placed around said inner semi-cylinder and fixed in a direction along the axis of said inner semi-cylinder between said handle and said collar, said outer partial cylinder being rotatable on said inner semi-cylinder, wherein said outer partial cylinder is configured to cover the first longitudinal opening in said inner semi-cylinder when said outer partial cylinder is rotated about the axis of said inner semi-cylindrical opening, whereby said applicator is enclosed within said inner semi-cylinder and said outer partial cylinder.

8. A single dose package as in claim 7 further comprising:

a plug recess formed in said material chamber opposing the opening;

a material placed in said material chamber; and a plug placed in said plug recess, whereby said material is sealed within said material well.

9. A single dose package as in claim 8 wherein:

said plug has an insert with a predetermined longitudinal length, whereby the predetermined longitudinal length of said insert is capable of being selected to adjust a volume of said material well.

10. A single dose package as in claim 7 further comprising:

a first planar surface formed on said material chamber.

11. A single dose package as in claim 10 further comprising:

indicia printed on said first planar surface.

12. A single dose package as in claim 7 further comprising:

further comprising a second planar surface formed on said outer partial cylinder.

13. A single dose package comprising:

a material chamber having an opening;

a handle attached to said material chamber covering the opening;

a frangible line placed between said material chamber and said handle;

an inner semi-cylinder attached to said handle, said inner semi-cylinder having an inner surface and a distal end;

a protuberance formed on the interior surface of said inner semi-cylinder;

an applicator placed within said inner semi-cylinder and held by said protuberance;

a collar formed on said distal end;

an outer partial cylinder having a longitudinal opening placed on said inner semi-cylinder between said handle and said collar, said outer partial cylinder being rotatable on said inner semi-cylinder, whereby said outer partial cylinder is capable of being rotated so as to cover an opening in said inner semi-cylinder enclosing said applicator;

a plug recess formed in said material chamber opposing the opening;

a material placed in said material chamber;

a plug placed in said plug recess, whereby said material is sealed within said material well; and wherein said plug recess comprises a plurality of steps of different diameters.

14. A single dose package as in claim 13 wherein:

said plug comprises a predetermined diameter, whereby the predetermined diameter is capable of being selected to adjust a volume of said material well when said plug is inserted into one of the plurality of steps of said plug recess.

15. A single dose package as in claim 13 wherein:

said plug comprises a plurality of levels of different diameters, whereby at least one of the plurality of levels is capable of being removed to adjust a volume of said material well when said plug is inserted in said plug recess.

* * * * *